(12) United States Patent
Saeed et al.

(10) Patent No.: US 11,379,981 B1
(45) Date of Patent: Jul. 5, 2022

(54) SYSTEMS AND METHODS FOR DIAGNOSING AUTISM SPECTRUM DISORDER USING FMRI DATA

(71) Applicants: Fahad Saeed, Miami, FL (US); Fahad Almuqhim, Miami, FL (US)

(72) Inventors: Fahad Saeed, Miami, FL (US); Fahad Almuqhim, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/340,602

(22) Filed: Jun. 7, 2021

(51) Int. Cl.
*G06T 7/00* (2017.01)
*A61B 5/055* (2006.01)

(52) U.S. Cl.
CPC ............ *G06T 7/0012* (2013.01); *A61B 5/055* (2013.01); *G06T 2207/10088* (2013.01); *G06T 2207/20081* (2013.01); *G06T 2207/20084* (2013.01); *G06T 2207/30016* (2013.01)

(58) Field of Classification Search
None
See application file for complete search history.

(56) References Cited

U.S. PATENT DOCUMENTS

| | | | |
|---|---|---|---|
| 11,096,583 B2 * | 8/2021 | Emerson | A61B 5/4064 |
| 2017/0261584 A1 * | 9/2017 | James | G01R 33/4818 |
| 2019/0133446 A1 * | 5/2019 | Emerson | G01R 33/4806 |
| 2019/0148021 A1 * | 5/2019 | Styner | A61B 5/7267 705/2 |
| 2021/0034912 A1 * | 2/2021 | Lisi | G06T 7/0014 |

OTHER PUBLICATIONS

Guo, Xinyu, et al. "Diagnosing autism spectrum disorder from brain resting-state functional connectivity patterns using a deep neural network with a novel feature selection method." Frontiers in neuroscience 11 (2017): 460. (Year: 2017).*

Eslami, Taban, et al. "ASD—DiagNet: a hybrid learning approach for detection of autism spectrum disorder using fMRI data." Frontiers in neuroinformatics 13 (2019): 70. (Year: 2019).*

* cited by examiner

*Primary Examiner* — Samah A Beg
(74) *Attorney, Agent, or Firm* — Saliwanchik, Lloyd & Eisenschenk (57) ABSTRACT

Systems and methods for diagnosing autism spectrum disorder (ASD) using only functional magnetic resonance imaging (fMRI) data are provided. Machine learning infrastructure can be used to identify reliable biomarkers of ASD in order to classify patients with ASD from among a group of typical control subjects using only fMRI. A sparse autoencoder (SAE) can be used, resulting in optimized extraction of features that can be used for classification. These features can then be fed into a deep neural network (DNN), which results in classification of fMRI brain scans more prone to ASD. The model can be trained to optimize the classifier while improving extracted features based on both reconstructed data error and the classifier error.

20 Claims, 5 Drawing Sheets

| Site | MRI Scanner | TR (ms) | TE (ms) | Flip Angle (Degree) | Age (Year) |
|---|---|---|---|---|---|
| Caltech | SIEMENS | 2000 | 30 | 75 | 17 - 56.2 |
| CMU | SIEMENS | 2000 | 30 | 73 | 19-40 |
| KKI | PHILLIPS | 2500 | 30 | 75 | 8-12.8 |
| Leuven | PHILLIPS | 1656 | 33 | 90 | 12.1-32 |
| MaxMun | SIEMENS | 3000 | 30 | 80 | 7-58 |
| NYU | SIEMENS | 2000 | 15 | 90 | 6.5-39.1 |
| OHSU | SIEMENS | 2500 | 30 | 90 | 8-15.2 |
| OLIN | SIEMENS | 1500 | 27 | 60 | 10-24 |
| PITT | SIEMENS | 1500 | 25 | 70 | 9.3-35.2 |
| SBL | PHILLIPS | 2200 | 30 | 80 | 20-64 |
| SDSU | GE | 2000 | 30 | 90 | 8.7-17.2 |
| Stanford | GE | 2000 | 30 | 80 | 7.5-12.9 |
| Trinity | PHILLIPS | 2000 | 28 | 90 | 12-25.9 |
| UCLA | SIEMENS | 3000 | 28 | 90 | 8.4-17.9 |
| UM | GE | 2000 | 30 | 90 | 8.2-28.8 |
| USM | SIEMENS | 2000 | 28 | 90 | 8.8-50.2 |
| Yale | SIEMENS | 2000 | 25 | 60 | 7-17.8 |

FIG. 3

| Method | Accuracy | Sensitivity | Specificity | Running time |
|---|---|---|---|---|
| ASD-SAENet | 70.8 | 62.2 | 79.1 | 52.74 min |
| ASD-DiagNet (Eslami et al., 2019) | 70.3 | 68.3 | 72.2 | 41.14 min |
| Heinsfeld et al. (Heinsfeld et al., 2018) | 70 | 74 | 63 | 7 hr |

FIG. 4

| Site | Accuracy | Sensitivity | Specificity |
|---|---|---|---|
| Caltech | 56.7 | 68.3 | 45 |
| CMU | 70.6 | 93.3 | 46.6 |
| KKI | 72.6 | 60 | 82 |
| Leuven | 64.6 | 50.6 | 77.1 |
| MaxMun | 47.5 | 49 | 54 |
| NYU | 72 | 67.9 | 75 |
| OHSU | 72 | 50 | 90.3 |
| OLIN | 66.6 | 81.6 | 46.6 |
| PITT | 73.1 | 78.6 | 64.6 |
| SBL | 56.6 | 60 | 53.3 |
| SDSU | 64.2 | 53.3 | 65.9 |
| Stanford | 53.2 | 36.6 | 70 |
| Trinity | 57.5 | 48 | 64 |
| UCLA | 68.3 | 72.3 | 64.1 |
| UM | 67.8 | 79 | 58.3 |
| USM | 70 | 63.5 | 71.5 |
| Yale | 66 | 69.3 | 64 |
| Average | 64.6 | 63.6 | 64.2 |

FIG. 5

|  | Data size | | Accuracy | | |
| --- | --- | --- | --- | --- | --- |
| Site | ASD | Typical Control | ASD-SAENet | ASD-DiagNet (Eslami et al., 2019) | Heinsfeld et al. (Heinsfeld et al., 2018) |
| Caltech | 19 | 18 | 56.7 | 52.8 | 52.3 |
| CMU | 14 | 13 | 70.6 | 68.5 | 45.3 |
| KKI | 20 | 28 | 72.6 | 69.5 | 58.2 |
| Leuven | 29 | 34 | 64.6 | 61.3 | 51.8 |
| MaxMun | 24 | 28 | 47.5 | 48.6 | 54.3 |
| NYU | 75 | 100 | 72 | 68 | 64.5 |
| OHSU | 12 | 14 | 72 | 82 | 74 |
| OLIN | 19 | 15 | 66.6 | 65.1 | 44 |
| PITT | 29 | 27 | 73.1 | 67.8 | 59.8 |
| SBL | 15 | 15 | 56.6 | 51.6 | 46.6 |
| SDSU | 14 | 22 | 64.2 | 63 | 63.6 |
| Stanford | 19 | 20 | 53.2 | 64.2 | 48.5 |
| Trinity | 22 | 25 | 57.5 | 54.1 | 61 |
| UCLA | 54 | 44 | 68.3 | 73.2 | 57.7 |
| UM | 66 | 74 | 67.8 | 64.2 | 57.6 |
| USM | 46 | 25 | 70 | 68.2 | 62 |
| Yale | 28 | 28 | 66 | 63.8 | 57.6 |
| Average | | | 64.6 | 63.8 | 56.1 |

FIG. 6

SYSTEMS AND METHODS FOR DIAGNOSING AUTISM SPECTRUM DISORDER USING FMRI DATA

GOVERNMENT SUPPORT

This invention was made with government support under R01GM134384 awarded by National Institute of Health (NIH). The government has certain rights in the invention.

BACKGROUND

More than 1.5 Million children in the United States are affected by Autism spectrum disorder (ASD), which is a heterogeneous neurodevelopmental disorder that is characterized by impaired social interactions, limited communication (including verbal and non-verbal), and/or exhibiting repeated or limited interests or activities. Individuals with ASD have numerous challenges in daily life, and they often develop comorbidities such as depression, anxiety disorder, or attention deficit hyperactivity disorder (ADHD), which may further complicate the diagnostic processes especially for young children. Although some symptoms are generally recognized between 1 or 2 years of age, numerous children are not formally diagnosed with ASD until they are much older. ASD is currently diagnosed via a psychiatric diagnostic process, which is based exclusively on behavioral observation of symptomology. This process is prone to misdiagnosis, especially in the presence of co-occurring and/or alternative diagnoses.

BRIEF SUMMARY

In view of the issues with the current diagnosis process for autism spectrum disorder (ASD), there is a need in the art for a more quantitative diagnosis. In order to address this, embodiments of the subject invention provide novel and advantageous systems and methods for diagnosing ASD using only functional magnetic resonance imaging (fMRI) data. Advanced and scalable machine learning infrastructure can be used to identify reliable biomarkers of ASD in order to classify patients with ASD from among a group of typical control subjects using only fMRI. A sparse autoencoder (SAE) can be used, resulting in optimized extraction of features that can be used for classification. These features can then be fed into a deep neural network (DNN), which results in superior classification of fMRI brain scans more prone to ASD. The model used with systems and methods of embodiments of the subject invention can be trained to optimize the classifier while improving extracted features based on both reconstructed data error and the classifier error.

In an embodiment, a system for diagnosing ASD (e.g., in a patient or a plurality of patients (i.e., classifying patients from among a group as either having ASD or not)) can comprise a processor and a (non-transitory) machine-readable medium in operable communication with the processor and having instructions stored thereon that, when executed by the processor, perform the following steps: receiving fMRI data (e.g., from a database, from a server or other computing device, or from an MRI machine that is a part of the system or with which the system is in operable communication) comprising a plurality of brain scans obtained from a plurality of patients, respectively; using a SAE on the fMRI data to extract testing patterns and generate a testing feature vector; providing the testing feature vector as a testing input to a DNN; and running the DNN on the testing feature vector to determine which brain scans of the plurality of brain scans are indicative of ASD, said brain scans that are indicative of ASD thereby resulting in a diagnosis of ASD in the corresponding patients, of the plurality of patients, from which said brain scans were obtained. The DNN can comprise two hidden layers, a softmax output layer, and/or an input layer. The instructions when executed can further performing the following step(s): training the SAE prior to using the SAE to extract testing patterns and generate the testing feature vector; and/or training the DNN prior to running the DNN on the testing feature vector. The training of the SAE and the training of the DNN can be performed simultaneously. The training of the SAE and the training of the DNN can comprise running a predetermined number of iterations of training on the SAE and the DNN (see also FIG. 2B), each iteration comprising: i) extracting time series from the fMRI data; ii) calculating Pearson's correlations on the time series; iii) selecting ¼ smallest and ¼ largest average pairwise correlations of the Pearson's correlations to generate a training feature vector and a SAE loss; iv) providing the training feature vector as a training input to the DNN; v) running the DNN on the training feature vector to generate a prediction loss; vi) combining the SAE loss and the prediction loss to generate a total loss; vii) providing the total loss to the SAE and the DNN; and viii) returning to step i). The predetermined number of iterations can be, for example, at least 30. The DNN can (alternatively) be a pre-trained DNN. The SAE can comprise a cost function comprising a mean squared error, a weight decay, and a sparsity term. The training of the SAE (prior to using the SAE to extract testing patterns and generate the testing feature vector) can comprise minimizing the cost function of the SAE.

In another embodiment, a method for diagnosing ASD can comprise: receiving (e.g., by a processor) fMRI data (e.g., from a database, from a server or other computing device, or from an MM machine in operable communication with the processor) comprising a plurality of brain scans obtained from a plurality of patients, respectively; using (e.g., by the processor) a SAE on the fMRI data to extract testing patterns and generate a testing feature vector; providing (e.g., by the processor) the testing feature vector as a testing input to a DNN; and running (e.g., by the processor) the DNN on the testing feature vector to determine which brain scans of the plurality of brain scans are indicative of ASD, said brain scans that are indicative of ASD thereby resulting in a diagnosis of ASD in the corresponding patients, of the plurality of patients, from which said brain scans were obtained. The DNN can comprise two hidden layers, a softmax output layer, and/or an input layer. The method can further comprise: training (e.g., by the processor) the SAE prior to using the SAE to extract testing patterns and generate the testing feature vector; and/or training (e.g., by the processor) the DNN prior to running the DNN on the testing feature vector. The training of the SAE and the training of the DNN can be performed simultaneously. The training of the SAE and the training of the DNN can comprise running (e.g., by the processor) a predetermined number of iterations of training on the SAE and the DNN (see also FIG. 2B), each iteration comprising: i) extracting time series from the fMRI data; ii) calculating Pearson's correlations on the time series; iii) selecting ¼ smallest and ¼ largest average pairwise correlations of the Pearson's correlations to generate a training feature vector and a SAE loss; iv) providing the training feature vector as a training input to the DNN; v) running the DNN on the training feature vector to generate a prediction loss; vi)

combining the SAE loss and the prediction loss to generate a total loss; vii) providing the total loss to the SAE and the DNN; and viii) returning to step i). The predetermined number of iterations can be, for example, at least 30. The DNN can (alternatively) be a pre-trained DNN. The SAE can comprise a cost function comprising a mean squared error, a weight decay, and a sparsity term. The training of the SAE (prior to using the SAE to extract testing patterns and generate the testing feature vector) can comprise minimizing the cost function of the SAE.

DETAILED DESCRIPTION

Embodiments of the subject invention provide novel and advantageous systems and methods for diagnosing autism spectrum disorder (ASD) using only functional magnetic resonance imaging (fMRI) data. Advanced and scalable machine learning infrastructure can be used to identify reliable biomarkers of ASD in order to classify patients with ASD from among a group of typical control subjects using only fMRI. A sparse autoencoder (SAE) can be used, resulting in optimized extraction of features that can be used for classification. These features can then be fed into a deep neural network (DNN), which results in superior classification of fMRI brain scans more prone to ASD. The model used with systems and methods of embodiments of the subject invention can be trained to optimize the classifier while improving extracted features based on both reconstructed data error and the classifier error.

In order to reduce the dimensionality of the input, a SAE model can be used to extract useful patterns with lower dimensionality to be the feature vector to the DNN. The DNN can include two hidden layers and a softmax output layer. The SAE can be trained to minimize its cost function, and the DNN classifier can be trained by taking the bottleneck of the SAE as inputs. The SAE and the classifier can be trained simultaneously.

Related art diagnostic processes for ASD are based purely on behavioral descriptions of symptomology (DSM-5/ICD-10) from informants observing children with the disorder across different settings (e.g., home, school). Early cognitive, language, and social interventions for children (under 24 months old) with ASD can be especially effective, and a delayed diagnosis can have more negative effects in the life of the child. Assisted learning or speech therapies are often available to these children (especially in low-income demographics), yet only after a diagnosis has been administered, making an early diagnosis even more important and beneficial. ASD results from altered brain development in the early childhood, but there are no related art processes that utilize reliable biomarkers for diagnosis. The shortcomings of related art clinical approaches and the poor understanding of the neurological mechanisms emphasize the advantages of embodiments of the subject invention, which build off identification of new biomarkers and computational techniques that can aid clinicians and neuroscientists alike to understand the distinct way an ASD brain works as compared to a typical brain.

Advances in neuroimaging technologies provide a critical step and help make it possible to measure functional and structural changes associated with ASD of the brain. fMRI can be used to detect biomarker patterns for brain disorders, and resting state fMRI (rs-fMRI), which is scanning the subjects while resting, can capture useful information while taking less scan time than other modalities while better demonstrating functional connectivity in the brain (see, e.g., Lau et al., Resting-state abnormalities in autism spectrum disorders: a meta-analysis, Scientific reports 9, 1-8, 2019; which is hereby incorporated by reference herein in its entirety). Detecting and finding optimal biomarkers from imaging datasets such as fMRI has attracted significant attention in recent years. One of the key reasons for this increased attention is the availability of publicly accessible Autism Brain Imaging Data Exchange (ABIDE) datasets collected from 17 different sites (see Craddock et al., The neuro bureau preprocessing initiative: open sharing of preprocessed neuroimaging data and derivatives, Neuroinformatics 4, 2013; which is hereby incorporated by reference herein in its entirety). The ABIDE dataset includes 1,035 rs-fMRI data from 505 ASD subjects and 530 TC subjects, collected from 17 different sites.

Embodiments of the subject invention provide machine-learning models that can distinguish and classify fMRI data from ASD subjects, and from typical control (TC) subjects. A deep learning algorithm can extract and distinguish between the functional features associated with ASD fMRI brain scans. Machine-learning, especially deep-learning models, is very useful for making sense of complex imaging datasets. A SAE can be used and can lower the dimensionality of the input features. The sparsity of the SAE helps in extracting the feature from high-dimensional imaging data while ensuring that limited sample size does not lead to overfitting. Extraction of feature(s) can then be followed by a DNN with two hidden layers and a softmax layer at the output. Embodiments of the subject invention can achieve a good accuracy (e.g., 70.2% or more).

fMRI is a brain imaging that is used to capture the brain image over time. The data of fMRI is represented by measuring the blood-oxygen-level-dependent (BOLD) volume of each small cubic called voxel at a time point. Thus, the data includes a time series of each voxel representing its activity over time. For brain disorders, resting state fMRI (rs-fMRI) is commonly used, which is scanning the brain image while the subject is resting.

Craddock 200 (CC200) (see Craddock et al., A whole brain fmri atlas generated via spatially constrained spectral clustering, Human brain mapping 33, 1914-1928, 2012; which is hereby incorporated by reference herein in its entirety) atlas divides the brain into 200 regions. Time series of each region can be extracted. The Pearson's correlation coefficient can be used to calculate the functional correlations of the regions of interest (ROIs). The following equation shows how to obtain the correlation between two different regions given the time series of each region, i and j, of length T $$p_{i,j} = \frac{\sum_{t=1}^{T}(i_t - \bar{i})(j_t - \bar{j})}{\sqrt{\sum_{t=1}^{T}(i_t - \bar{i})^2} \sqrt{\sum_{t=1}^{T}(j_t - \bar{j})^2}} \quad (1)$$

where i and j are the mean of the time series i and the mean of the time series j, respectively. A matrix $C_{n*n}$ can be obtained after computing all pair correlations. If CC200 atlas is used, which divides the brain into n=200 regions, a matrix of 200 by 200 is generated. Due to the symmetry of the matrix with regard to the diagonal, only the right upper triangle of the matrix needs be considered, and it can be flattened to a one-dimensional vector as the features. These pairs result to have (n)(n−1)/2=19900 values for each vector. In order to reduce the dimensionality of the input, the same technique from Eslami et al. (supra.) can be adopted, and only the ¼ largest and ¼ smallest of the average correlations need be considered, resulting in a vector of 9950 values as the input for each subject.

In order to reduce the dimensionality of the input, an autoencoder model was developed. The autoencoder (AE) neural network is unsupervised learning that uses a feed-forward neural network with an encoding and decoding architecture. It can be trained to get an input x and then reconstruct x' to be as similar to the input x as possible. There are several types of autoencoders, such as SAE (see Ng et al., Sparse autoencoder, CS294A, Lecture notes 72, 1-19, 2011; which is hereby incorporated by reference herein in its entirety), a stacked autoencoder (see Vincent et al., Stacked denoising autoencoders: Learning useful representations in a deep network with a local denoising criterion, Journal of machine learning research, 11, 2010; which is hereby incorporated by reference herein in its entirety), and a denoising autoencoder (see Vincent et al., Extracting and composing robust features with denoising autoencoders, In Proceedings of the 25th international conference on Machine learning, 1096-1103, 2008; which is hereby incorporated by reference herein in its entirety). Autoencoders can fail to reconstruct the raw data because it might fall into a copying task especially when there is a large data space. Using a SAE forces the autoencoder to reconstruct the raw data from useful features rather than copying data (see also Goodfellow et al., Deep learning, vol. 1 (MIT press Cambridge), 2016; which is hereby incorporated by reference herein in its entirety). In this case, a SAE can be used to extract useful patterns with lower dimensionality to be the feature vector to the DNN model, which can include (or even consist of) two hidden layers and a softmax output layer.

Figure 1:
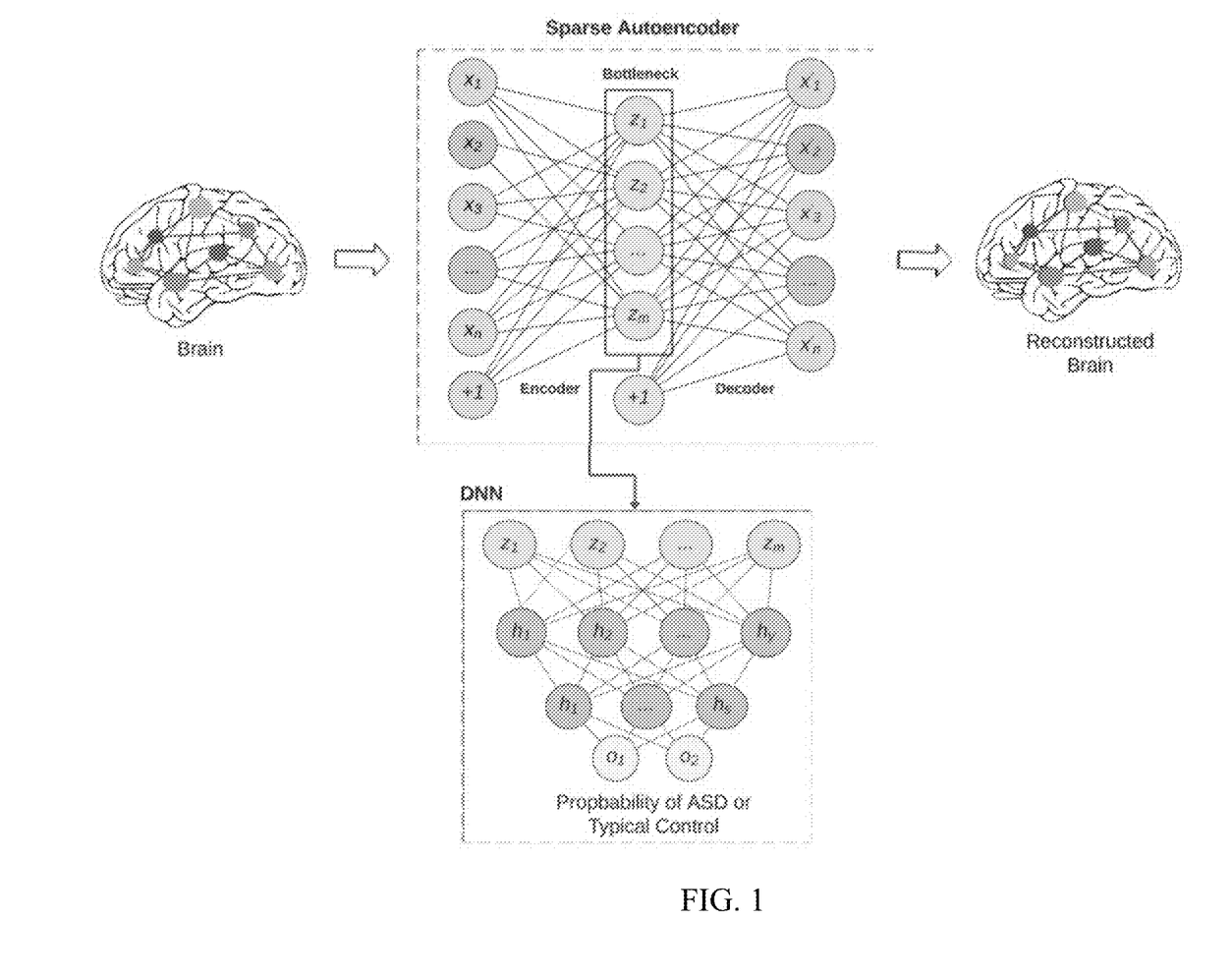
FIG. 1 shows a schematic view of a model that can be used with systems and methods according to embodiments of the subject invention. The sparse autoencoder (SAE) can be used as feature selection for a deep neural network (DNN).

FIG. 1 shows a schematic view of an overview of a model that can be used with embodiments of the subject invention. The model can be referred to herein as "ASD-SAENet". Referring to FIG. 1, the bottleneck of the SAE can be used as an input vector to the DNN. In FIG. 1, neurons labeled as (+1) are the bias units added to the feed-forward neural network through the cost function. This step will force the AE to better reconstruct the input x without falling into overfitting. The cost function of the SAE can include three parts that can help avoid overfitting when encoding and decoding the input data.

Given a dataset of N training samples $(x_1, x_2, \ldots, x_n)$, where $x_i$ represents the $i^{th}$ input, the SAE can be trained to reconstruct the input $x_i$ with the function $h_{W,b}(x_i)$ to be as close to $x_i$ as possible. The three parts of the cost function can be mean squared error, weight decay, and sparsity term. The first two parts of the cost function, the mean squared error of all N training samples, and the weight decay can be defined as follows:

$$J_{sparse}(W, b) = \frac{1}{N}\sum_{i=1}^{N}\frac{1}{2}\|h_{W,b}(x^i) - x^i\| \quad (2)$$

$$+ \frac{\lambda}{2}\sum_{l=1}^{n_l-1}\sum_{i=1}^{s_l}\sum_{j=1}^{s_{l+1}}(W_{ji}^l)^2 \quad (3)$$

Equation 3 defines the weight decay, which helps to avoid overfitting. A small value of λ may lead to overfitting, while a large value of λ may lead to underfitting. Thus, several values of λ were utilized to achieve the best fit of this term.

The third part of the cost function is the sparsity term, which is used to apply activations to the hidden layer of the AE model to prevent or inhibit overfitting. It can limit the number of regions that are considered in the hidden layer. The following equation defines the average activated value of the hidden layer, where a denotes the activation function, which is a rectified linear activation function (ReLU):

$$\hat{p}_j = \frac{1}{N}\sum_{i=1}^{N}(a_j^2(x^i)) \quad (4)$$

The sparsity term can be calculated to make $\hat{p}_j$ as close to p as possible, where p is the sparsity parameter. The benefit of this parameter is that if $\hat{p}_j$ deviates from p, it will activate and deactivate neurons on the hidden layer. This term is defined using Kullback-Leibler divergence as follows:

$$\sum_{j=1}^{s_l} KL(p \| \hat{p}_j) = \sum_{j=1}^{s_l} \left[ p \log \frac{p}{\hat{p}_j} + (1-p) \log \frac{1-p}{1-\hat{p}_j} \right] \quad (5)$$

The cost function of the SAE model after adding all the three parts is defined as follows:

$$J_{sparse}(W, b) = \quad (6)$$

$$\frac{1}{N} \sum_{i=1}^{N} \frac{1}{2} \| h_{W,b}(x^i) - x^i \| + \frac{\lambda}{2} \sum_{l=1}^{n_l-1} \sum_{i=1}^{s_l} \sum_{j=1}^{s_{l+1}} (W_{ji}^l)^2 + \beta \sum_{j=1}^{s_l} KL(p \| \hat{p}_j)$$

where $\beta$ is the sparse penalty term.

The SAE is used to reduce the dimensional representation of the input. The bottleneck of the SAE provides useful features that can be used as inputs for the DNN classifier. The classifier can include two hidden layers and an output layer, which can be a softmax regression (see Goodfellow et al., 6.2. 2.3 softmax units for multinoulli output distribution, In Deep Learning (MIT Press), 180-184, 2016; which is hereby incorporated by reference herein in its entirety), which represents the probability of each class. In order to avoid overfitting, a dropout can be used between the fully connected neural networks. Then, the maximum probability between the two classes can be taken as the final decision of the classifier. Cross entropy can be used for calculating the cost function of the classifier, and the weight decay term can be added.

The model can start with taking all the selected features as inputs to the SAE with a bottleneck size of hidden units, which can be then fed into the DNN classifier. The DNN classifier can include an input layer, two hidden layers, and a softmax layer (e.g., with units of, for example, 4975, 2487, 500, and 2, respectively). The SAE can be trained to minimize its cost function, and the DNN classifier can be trained by taking the bottleneck of the SAE as inputs. The SAE and the classifier can be trained simultaneously, though embodiments are not limited thereto. With simultaneous training, the feature extraction can be improved while optimizing the classifier's decision. The training process can be completed in a set number of iterations (e.g., 30 iterations) with a set batch size (e.g., batch size of 8). The sparsity parameter p, the weight decay $\lambda$, and the sparse penalty term $\beta$ can be chosen with predetermined values (e.g., 0.05, 0.0001, and 2, respectively). The DNN classifier can be fine-tuned (e.g., on the last 10 iterations) to adjust the parameters of the classifier and minimize the cost function of the softmax (e.g., while the parameters of SAE are frozen). An optimizer can optionally be used to update the parameters based on the computed gradients.

Figure 2A:
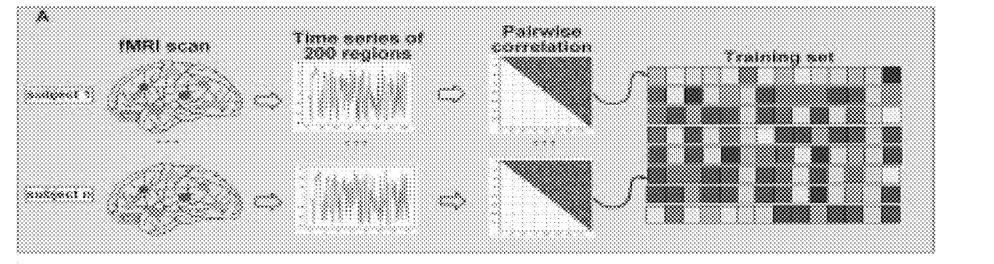
FIG. 2A shows pre-processing steps for a model that can be used with systems and methods according to embodiments of the subject invention. The pre-processing steps can include extracting time series from functional magnetic resonance imaging (fMRI) scans, calculating the Pearson's correlations, and selecting ¼ smallest and largest average pairwise correlations for feature vectors.
Figure 2B:
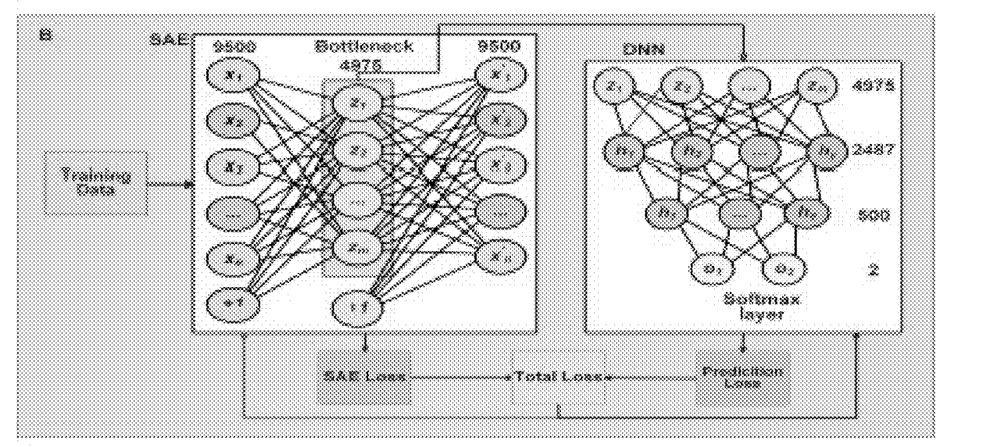
FIG. 2B shows a schematic view illustrating how a model, which can be used with systems and methods according to embodiments of the subject invention, is trained at the same time to improve feature selection while obtaining an optimal classification model. The DNN classifier input can be the bottleneck of the SAE.
Figure 2C:
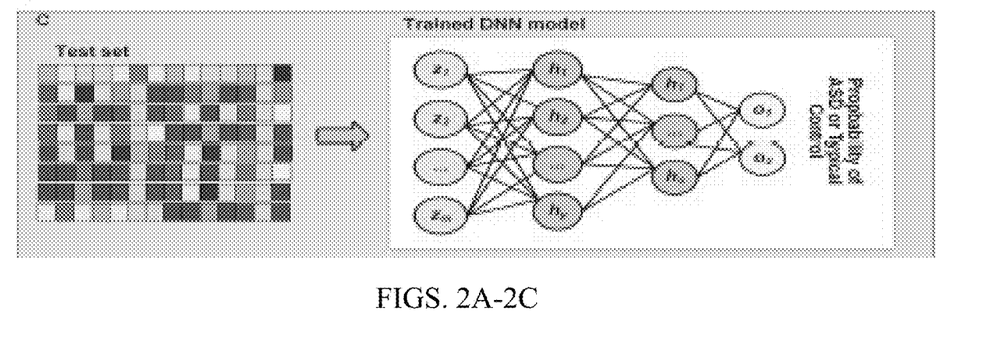
FIG. 2C shows a testing process where the input subject is fed into the trained SAE, and then the DNN can take the bottleneck to make the classification using a softmax layer.

FIGS. 2A-2C show the ASD-SAENet model, which can be used with embodiments of the subject invention. FIG. 2A shows pre-processing steps for the model, and the pre-processing steps can include extracting time series from functional magnetic resonance imaging (fMRI) scans, calculating the Pearson's correlations, and selecting ¼ smallest and largest average pairwise correlations for feature vectors. FIG. 2B shows how the model can be trained at the same time to improve feature selection while obtaining an optimal classification model. The DNN classifier input can be the bottleneck of the SAE. FIG. 2C shows a testing process where the input subject is fed into the trained SAE, and then the DNN can take the bottleneck to make the classification using a softmax layer.

Embodiments of the subject invention provide deep-learning systems and methods for classifying brain scans that exhibit ASD (and distinguishing the same from healthy control scans). The systems and methods can utilized SAEs, which are not used in any related art system or method. SAEs are more open to interpretability, which can advance the understanding of the neurobiological underpinning of the ASD brain. The Pearson's correlations of data regions of the brain can be used as features that are fed into a SAE to lower the dimensionality of the features. These features can then be fed to the DNN that can have two hidden layers and a softmax function as an output layer. The SAE and the DNN can be trained simultaneously for feature selection and improving classifier decision. In some embodiments, further training to improve the classifier can be done by executing more iterations with the AE kept at a constant state. The results from the examples show significant improvements over state-of-the-art, related art methods. The SAE, coupled with the limited amount of fMRI data that is available for ASD, demonstrates a computationally light-weight machine-learning module for ASD identification and classification.

Embodiments of the subject invention address the technical problem of quantitatively and accurately diagnosing ASD by providing the technical solution of using a SAE and a DNN, with the feature vector of the SAE being the input to the DNN, thereby accurately diagnosing ASD with only fMRI data.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., sub-ranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Materials and Methods

Figure 3:
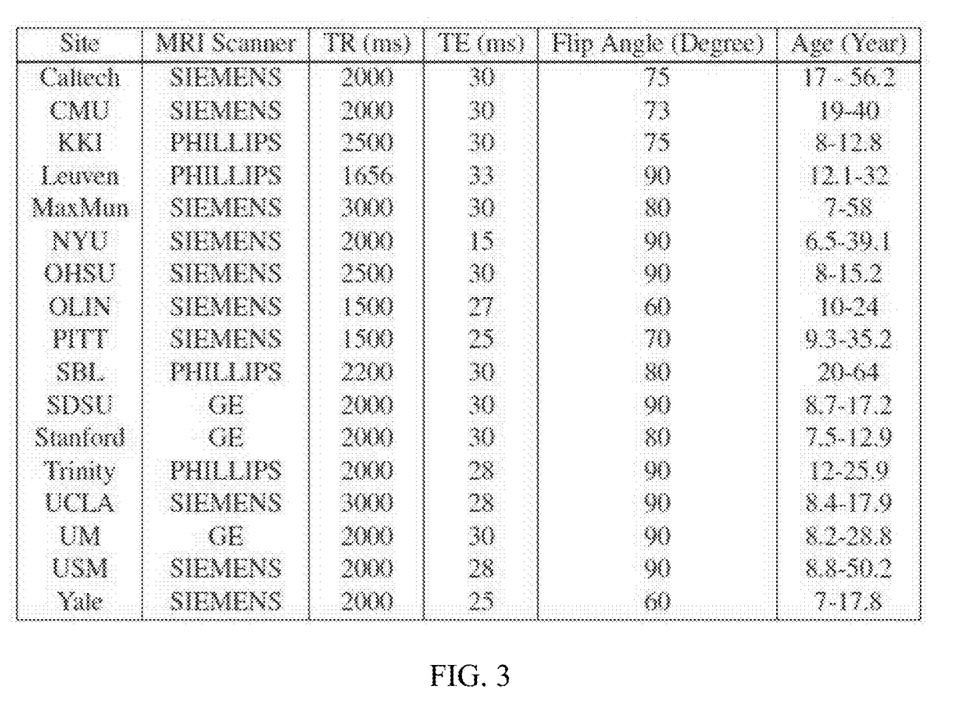
FIG. 3 shows a table with scanning parameters of each site of a plurality of sites used for testing.

The ABIDE dataset was used for testing. The dataset was pre-processed using the Configurable Pipeline for the Analysis of Connectomes C-PAC pipeline (see Craddock et al., 2013, supra.), which is parcellated into 200 region of interests (ROIs) using Craddock 200 (CC200) functional parcellation (see Craddock et al., 2012, supra.). For each region, the average voxels' BOLDs were calculated. The pre-processing steps also included skull-striping, slice time correction, motion correction, and nuisance signal regression. Each site used different parameters, and scanners for brain imaging, such as repetition time (TR), echo time (TE), and flip angle degree. FIG. 3 shows the parameters of each site.

Because CC200 atlas was used and divided the brain into n=200 regions, a matrix of 200 by 200 was generated. Due to the symmetry of the matrix with regard to the diagonal, only the right upper triangle of the matrix was considered, and it was flattened to a one-dimensional vector as the features. These pairs resulted to have $(n)(n-1)/2=19,900$ values for each vector. In order to reduce the dimensionality of the input, the same technique from Eslami et al. (supra.) was adopted, and only the ¼ largest and ¼ smallest of the average correlations were considered, resulting in a vector of 9,950 values as the input for each subject.

The model started with taking all the 9,500 selected features as inputs to the SAE with a bottleneck size of 4,975 hidden units, which were then fed into the DNN classifier. The DNN classifier included an input layer, two hidden layers, and a softmax layer, where the units were 4975, 2487, 500, and 2 respectively. The SAE was trained to minimize its cost function, and the DNN classifier was trained by taking the bottleneck of the SAE as inputs. The SAE and the classifier were trained simultaneously. Thus, the feature extraction was improved while optimizing the classifier's decision. The training process was completed in 30 iterations, and the batch size was 8. The sparsity parameter p, the weight decay $\lambda$, and the sparse penalty term $\beta$ were chosen to be 0.05, 0.0001, and 2, respectively. The DNN classifier was fine-tuned on the last 10 iterations to adjust the parameters of the classifier and minimize the cost function of the softmax, while the parameters of SAE were frozen. Adam optimizer (see Kingma et al., Adam: A method for stochastic optimization, arXiv preprint arXiv:1412.6980, 2014; which is hereby incorporated by reference herein in its entirety) was used to update the parameters based on the computed gradients. The ASD-SAENet model can be seen in FIGS. 2A-2C. All of the example tests were performed using a Linux server with Ubuntu OS. The server had a processor of Intel Xeon E5-2690 v3 at 2.60 GHz. The total RAM was 54 GBs. The server also contained an NVIDIA Tesla K80 running CUDA version 10.2 and PyTorch library to perform the deep learning model.

Due to the limitation of the sample data, the model was evaluated using k-fold cross validation technique, in which the dataset is randomly split into k equal sized samples, and one of these is used for getting the classification performance. This process was repeated k times to ensure that the model is not overfitted (see Moore, Cross-validation for detecting and preventing overfitting, School of Computer Science Carnegie Mellon University, 2001; which is hereby incorporated by reference herein in its entirety).

In the experiments, ASD-SAENet was evaluated in two different scenarios. First, the whole dataset containing 1,035 subjects was used to evaluate the model, and then the model was tested on each site separately. Evaluating each site separately demonstrates how the model performs on small datasets and how it generalizes across different data acquisition sites and magnetic resonance imaging (MRI) machines.

Example 1—Average Accuracy on the ABIDE Dataset

Figure 4:
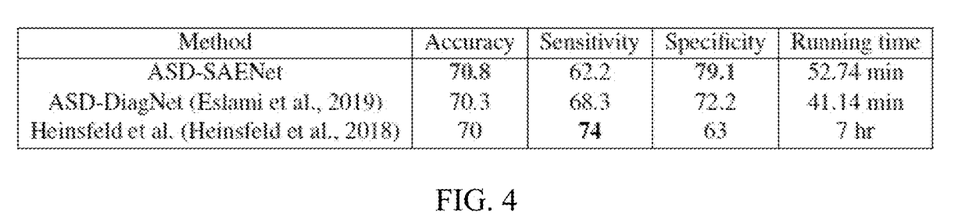
FIG. 4 shows a table with accuracy, sensitivity, specificity, and running time results for an embodiment of the subject invention (labeled "ASD-SAENet" in FIG. 4) and two related art methods. The "ASD-DiagNet" related art method is from Eslami et al. (Asd-diagnet: a hybrid learning approach for detection of autism spectrum disorder using fmri data, Frontiers in neuroinformatics 13, 70, 2019; which is hereby incorporated by reference herein in its entirety) and the "Heinsfeld et al." related art method is from Heinsfeld et al. (Identification of autism spectrum disorder using deep learning and the abide dataset, NeuroImage: Clinical 17, 16-23, 2018; which is hereby incorporated by reference herein in its entirety).

In this experiment, k was chosen as 10 to perform 10-fold cross validation using the whole dataset. The ASD-SAENet model was compared with the related art ASD-DiagNet model (Eslami et al., supra.) and the method proposed by Heinsfeld et al. (Heinsfeld et al., supra.). FIG. 4 shows the compression of accuracy, sensitivity, specificity, and the running time results of the comparison. Referring to FIG. 4, the result show that ASD-SAENet achieved 70.8% accuracy, which is comparable to the average accuracy of the state-of-the-art, related art methods.

Example 2—Accuracy for Each Data Acquisition Site

Figure 5:
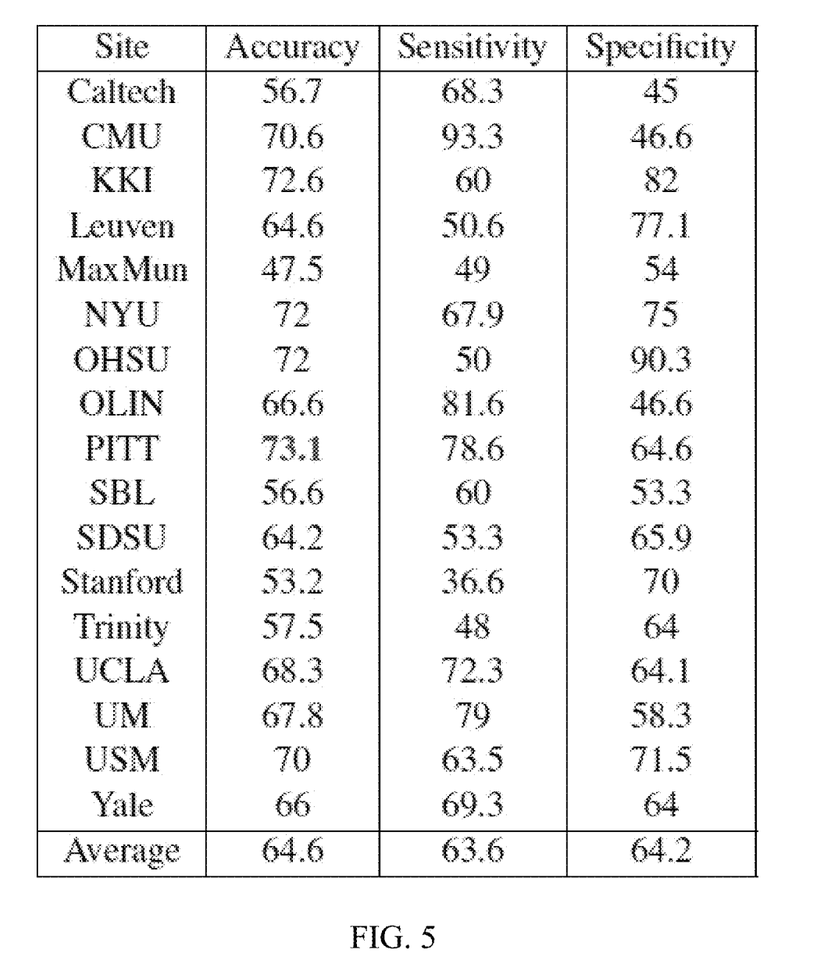
FIG. 5 shows a table with accuracy, sensitivity, and specificity values for each site of a plurality of sites used for testing.
Figure 6:
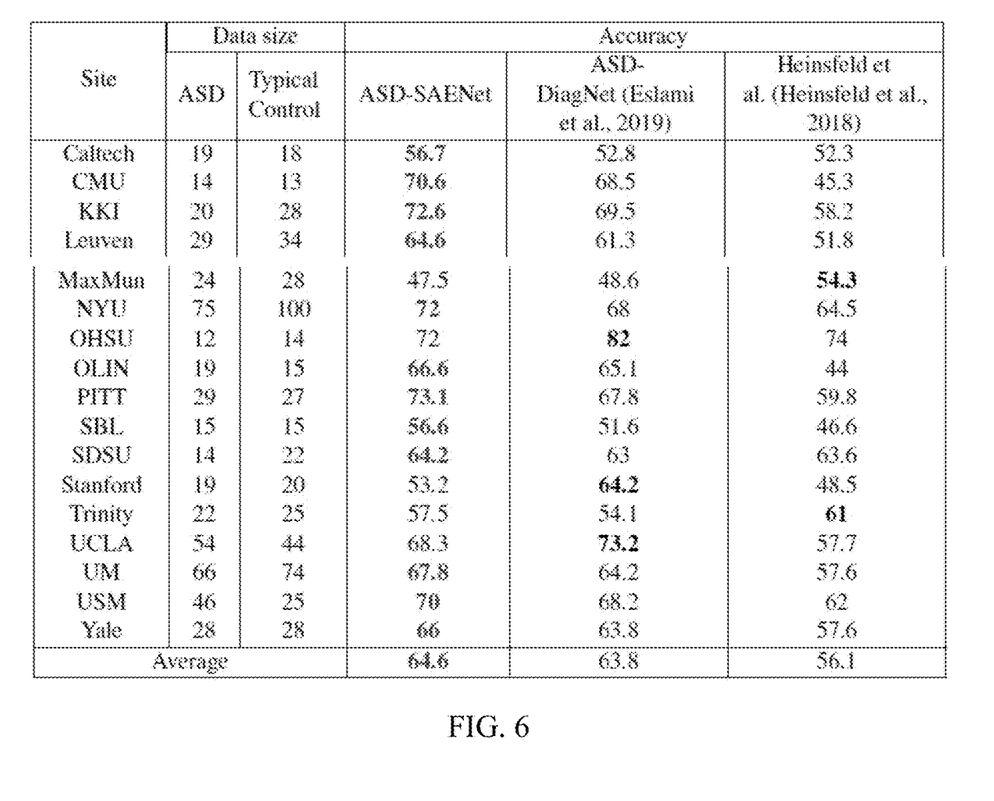
FIG. 6 shows a table with comparison results for an embodiment of the subject invention (labeled "ASD-SAENet" in FIG. 6) and two related art methods (labeled in FIG. 6 as "ASD-DiagNet" and "Heinsfeld et al.", which are the same as those discussed for FIG. 4) for each site of a plurality of sites used for testing.

In this experiment, a 5-fold cross validation for each site was performed because of the limitation of the size of the data. FIG. 5 shows the accuracy, sensitivity, and specificity results for ASD-SAENet for each site. FIG. 6 shows a comparison of the accuracy of ASD-SAENet with the state-of-the-art, related art methods, ASD-DiagNet (Eslami et al., supra.) and Heinsfeld et al. (Heinsfeld et al., supra.). Referring to FIGS. 5 and 6, these results demonstrate that the ASD-SAENet model outperformed the state-of-the-art, related art methods, and exhibited better accuracy with 12 out of the 17 sites. The average accuracy achieved by the ASD-SAENet model was 64.42%, which is comparable to the other tested methods as well. The fact that the ASD-SAENet model exhibits better accuracy for a higher number of sites compared to both state-of-the-art methods shows the robustness and generalizability of the ASD-SAENet model.

The results in the examples show differences in site-specific accuracies, which can explain that different scanners, parameters, and age range might affect the accuracy (e.g., different settings when scanning the brain may affect the result). For example, in the examples, the highest accuracy was on the PITT site dataset, which used a Siemens scanner, repetition time of 1500 milliseconds (ms), echo time of 25 ms, flip angle of 70 degrees, and an age range of 9.3 years-35.2 years. The lowest accuracy with almost similar data size was on the MaxMun dataset, which used the same MM scanner, different parameters (i.e., 3,000 ms for repetition time, 30 ms for echo time, and 80 for flip angle degree), and a huge gap of age range. This finding can show that a Siemens scanner should work well when the age range is not huge, and there is a correlation between echo time and flip angle degree. Moreover, considering the results of the other sites, it can be found that the parameters and scanners can affect the performance of the model. For example, most of the sites that achieved around 70% accuracy were using a Siemens scanner, repetition time of between 1500 ms and 2500 ms, and an age range that was not large. The results also demonstrate that there is a correlation between the echo time and the flip angle degree, where their sum should be between 95 and 105, like what were set in the NYU and PITT sites.

Overall, compared with the ASD-DiagNet model, the ASD-SAENet model exhibited similar accuracy (70.8% vs. 70.3%), superior specificity (79.1% vs. 72.2%), and slightly lower sensitivity (62.2% vs. 68.3%) is observed. This slight decrease in sensitivity can be attributed to the usage of the SAE, in which only a small number of the hidden units are allowed to be active at the same time and which may miss some features. However, the strength of the model outweighs the small decrease in the sensitivity by exhibiting superior specificity. This means that the number of true-negative rate is comparatively less than the related art methods, leading to classifiers that can be used in the real world (i.e., because most of the population does not have ASD, it is important to correctly classify people who do not have the condition (unaffected)). The additional advantages of the ASD-SAENet model are the unique statistical features and low computational cost, which will help in identifying feature importance estimates.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for diagnosing autism spectrum disorder (ASD), the system comprising:
    a processor; and
    a machine-readable medium in operable communication with the processor and having instructions stored thereon that, when executed by the processor, perform the following steps:
        receiving functional magnetic resonance imaging (fMRI) data comprising a plurality of brain scans obtained from a plurality of patients, respectively;
        using exactly one sparse autoencoder (SAE) on the fMRI data to extract testing patterns and generate a testing feature vector, the testing feature vector being generated using only the exactly one SAE;
        providing the testing feature vector as a testing input to a deep neural network (DNN); and
        running the DNN on the testing feature vector to determine which brain scans of the plurality of brain scans are indicative of ASD, said brain scans that are indicative of ASD thereby resulting in a diagnosis of ASD in the corresponding patients, of the plurality of patients, from which said brain scans were obtained.

2. The system according to claim 1, the DNN comprising two hidden layers and a softmax output layer.

3. The system according to claim 2, the DNN further comprising an input layer.

4. The system according to claim 1, the instructions when executed further performing the following step:
    training the exactly one SAE prior to using the exactly one SAE to extract testing patterns and generate the testing feature vector.

5. The system according to claim 4, the instructions when executed further performing the following step:
    training the DNN prior to running the DNN on the testing feature vector.

6. The system according to claim 5, the training of the exactly one SAE and the training of the DNN being performed simultaneously.

7. The system according to claim 6, the training of the exactly one SAE and the training of the DNN comprising running a predetermined number of iterations of training on the exactly one SAE and the DNN, each iteration comprising:
    i) extracting time series from the fMRI data;
    ii) calculating Pearson's correlations on the time series;
    iii) selecting ¼ smallest and ¼ largest average pairwise correlations of the Pearson's correlations to generate a training feature vector and a SAE loss;
    iv) providing the training feature vector as a training input to the DNN;
    v) running the DNN on the training feature vector to generate a prediction loss;
    vi) combining the SAE loss and the prediction loss to generate a total loss;
    vii) providing the total loss to the exactly one SAE and the DNN; and
    viii) returning to step i).

8. The system according to claim 7, the predetermined number of iterations being at least 30.

9. The system according to claim 1, the DNN being a pre-trained DNN.

10. The system according to claim 1, the exactly one SAE comprising a cost function comprising a mean squared error, a weight decay, and a sparsity term.

11. The system according to claim 10, the instructions when executed further performing the following step:
    training the exactly one SAE prior to using the exactly one SAE to extract testing patterns and generate the testing feature vector,
    the training of the exactly one SAE comprising minimizing the cost function of the exactly one SAE.

12. A method for diagnosing autism spectrum disorder (ASD), the method comprising:
    receiving, by a processor, functional magnetic resonance imaging (fMRI) data comprising a plurality of brain scans obtained from a plurality of patients, respectively;
    using, by the processor, exactly one sparse autoencoder (SAE) on the fMRI data to extract testing patterns and generate a testing feature vector, the testing feature vector being generated using only the exactly one SAE;

providing, by the processor, the testing feature vector as a testing input to a deep neural network (DNN); and running, by the processor, the DNN on the testing feature vector to determine which brain scans of the plurality of brain scans are indicative of ASD, said brain scans that are indicative of ASD thereby resulting in a diagnosis of ASD in the corresponding patients, of the plurality of patients, from which said brain scans were obtained.

13. The method according to claim 12, the DNN comprising an input layer, two hidden layers, and a softmax output layer.

14. The method according to claim 12, further comprising:

training, by the processor, the exactly one SAE prior to using the exactly one SAE to extract testing patterns and generate the testing feature vector; and training, by the processor, the DNN prior to running the DNN on the testing feature vector.

15. The method according to claim 14, the training of the exactly one SAE and the training of the DNN being performed simultaneously.

16. The method according to claim 15, the training of the exactly one SAE and the training of the DNN comprising running a predetermined number of iterations of training on the exactly one SAE and the DNN, each iteration comprising:

i) extracting time series from the fMRI data;
ii) calculating Pearson's correlations on the time series;
iii) selecting ¼ smallest and ¼ largest average pairwise correlations of the Pearson's correlations to generate a training feature vector and a SAE loss;
iv) providing the training feature vector as a training input to the DNN;
v) running the DNN on the training feature vector to generate a prediction loss;
vi) combining the SAE loss and the prediction loss to generate a total loss;
vii) providing the total loss to the exactly one SAE and the DNN; and
viii) returning to step i).

17. The method according to claim 16, the predetermined number of iterations being at least 30.

18. The method according to claim 12, the DNN being a pre-trained DNN.

19. The method according to claim 12, the exactly one SAE comprising a cost function comprising a mean squared error, a weight decay, and a sparsity term, the method further comprising training the exactly one SAE prior to using the exactly one SAE to extract testing patterns and generate the testing feature vector, and the training of the exactly one SAE comprising minimizing the cost function of the exactly one SAE.

20. A system for diagnosing autism spectrum disorder (ASD), the system comprising:

a processor; and a machine-readable medium in operable communication with the processor and having instructions stored thereon that, when executed by the processor, perform the following steps:

receiving functional magnetic resonance imaging (fMRI) data comprising a plurality of brain scans obtained from a plurality of patients, respectively;

using exactly one sparse autoencoder (SAE) on the fMRI data to extract testing patterns and generate a testing feature vector, the testing feature vector being generated using only the exactly one SAE;

providing the testing feature vector as a testing input to a deep neural network (DNN); and running the DNN on the testing feature vector to determine which brain scans of the plurality of brain scans are indicative of ASD, said brain scans that are indicative of ASD thereby resulting in a diagnosis of ASD in the corresponding patients, of the plurality of patients, from which said brain scans were obtained, the DNN comprising an input layer, two hidden layers, and a softmax output layer, the instructions when executed further performing the following steps:

training the exactly one SAE prior to using the exactly one SAE to extract testing patterns and generate the testing feature vector; and training the DNN prior to running the DNN on the testing feature vector, the training of the exactly one SAE and the training of the DNN being performed simultaneously, the training of the exactly one SAE and the training of the DNN comprising running a predetermined number of iterations of training on the exactly one SAE and the DNN, each iteration comprising:

i) extracting time series from the fMRI data;
ii) calculating Pearson's correlations on the time series;
iii) selecting ¼ smallest and ¼ largest average pairwise correlations of the Pearson's correlations to generate a training feature vector and a SAE loss;
iv) providing the training feature vector as a training input to the DNN;
v) running the DNN on the training feature vector to generate a prediction loss;
vi) combining the SAE loss and the prediction loss to generate a total loss;
vii) providing the total loss to the exactly one SAE and the DNN; and
viii) returning to step i), the predetermined number of iterations being at least 30, the exactly one SAE comprising a cost function comprising a mean squared error, a weight decay, and a sparsity term, and the training of the exactly one SAE comprising minimizing the cost function of the exactly one SAE.

* * * * *